United States Patent [19]

Gorssman et al.

[11] Patent Number: 4,963,127

[45] Date of Patent: Oct. 16, 1990

[54] STANNIC TEREPHTHALATE

[75] Inventors: Richard F. Gorssman, Shelton, Conn.; David M. Tanno, Richmond Heights, Ohio

[73] Assignee: Synthetic Products Company, Cleveland, Ohio

[21] Appl. No.: 357,612

[22] Filed: May 24, 1989

Related U.S. Application Data

[63] Continuation of Ser. No. 226,318, Jul. 27, 1988, abandoned.

[51] Int. Cl.$^5$ .............................................. C07F 7/22
[52] U.S. Cl. ................................................... 556/106
[58] Field of Search ....................................... 556/106

[56] References Cited

U.S. PATENT DOCUMENTS

| | | | |
|---|---|---|---|
| 2,280,474 | 4/1942 | Byrkit et al. | 556/106 X |
| 2,355,240 | 8/1944 | Reiff | 556/106 X |
| 3,314,919 | 4/1967 | Most | 260/45.85 |
| 3,674,894 | 7/1972 | Economy | 260/875 |
| 3,884,825 | 5/1975 | Lindblad et al. | 252/62.1 |
| 3,973,982 | 8/1976 | Bingham | 106/298 |
| 4,039,515 | 8/1977 | Rebhan et al. | 260/75 |
| 4,096,109 | 6/1978 | Watanabe et al. | 260/40 |
| 4,101,523 | 7/1978 | Watanabe et al. | 528/309 |
| 4,198,458 | 4/1980 | Mitsuishi et al. | 428/212 |

*Primary Examiner*—Paul F. Shaver
*Attorney, Agent, or Firm*—Wood, Herron & Evans

[57] ABSTRACT

Stannic terephthalate has been prepared and has been found to have an unusually high dielectric constant, electrical and thermal stabilities, and high volume resistivity that make this compound ideal for use as a capacitor dielectric.

1 Claim, No Drawings

STANNIC TEREPHTHALATE

This application is a continuation, of application Ser. No. 226,318, filed July 27, 1988, now abandoned.

BACKGROUND OF THE INVENTION

Numerous metal salts of terephthalic acid have been reported in the literature with a broad range of utilities, most often as additives to polymeric compositions. For example, in U.S. Pat. No. 3,314,919 terephthalates of calcium, barium, manganese, zinc and cadmium were reportedly prepared and incorporated into textile fibers for the improvement of mechanical properties of such fibers. Other examples of patent literature disclosing metal terephthalates, principally in polymeric compositions, include U.S. Pat. Nos. 3,674,894; 3,884,825; 3,973,982; 4,039,515; 4,096,109; 4,101,523; 4,198,458 and others. Other literature has reported upon metal terephthalates and study of their various properties, but delineation of details of such studies are not considered to be relevant to the subject matter of this invention.

SUMMARY OF THE INVENTION

This invention is directed to a new metal salt of terephthalic acid, specifically stannic terephthalate. Stannic terephthalate has been prepared and it has been found that this compound has an unusually high dielectric constant. Moreover, it has been found that its electrical property is highly stable with regard to applied voltage and incident temperature. The combination of high dielectric constant, electrical and thermal stabilities, and high volume resistivity make this compound ideal for use as a capacitor dielectric.

DETAILED DESCRIPTION

A. Preparation of Stannic Terephthalate

A solution was prepared containing 383 grams of 50% sodium hydroxide in seven liters of water. To this solution was added 400 grams of terephthalic acid thereby producing a solution of sodium terephthalate. A solution of stannic chloride was prepared by adding 342 grams of stannic chloride to 0.4 liter water. The stannic chloride solution was then added to the sodium terephthalate solution at about 50° C. with continuous agitation, causing the development of a white precipitate. The precipitate was filtered, washed with water and dried. The stannic terephthalate produced by the above method was analyzed at 26.8% Sn; 42.5% C; 1.65% H. This analysis is within the experimental error of stannic terephthalate, i.e., $Sn(C_8H_4O_4)_2$ formula which theoretically provides 26.7% Sn, 42.8% C and 1.8% H. Thermogravimetric analysis for the stannic terephthalate indicated decomposition at 360° C. to a residue of $SnO_2$. The infrared spectrum of this salt, obtained in a KBr showed strong carbon-oxygen stretching absorption at 1685 and 1290/cm, typical of metal carboxylates having the $M+(C=O)O-$structure.

Samples of the prepared stannic terephthalate were compacted into flat plates of 10 mils in thickness and 3.5 cm radius at room temperature between polished steel plates at 20,000 psi in a laboratory press. Volume resistivity was determined using an Associated Research, inc. Model 2850 megohm bridge. Dielectric constant was determined using a Sprague Electric Model 16 capacitance bridge. The stannic (IV) terephthalate yielded a volume resistivity of $10^{12}$ ohm-cm and surprisingly had a dielectric constant in the range of 250. The exact value of the dielectric constant will vary with sample preparation and crystal form as it should be understood when the dielectric constant becomes large. In practice, therefore, the dielectric constant of this salt may vary from about 50 to several hundred or perhaps higher. The value obtained by the above technique was unchanged when the voltage applied across the sample was varied from 0 to 500 volts DC. Cycling to 300° C. led to a 10% increase in dielectric constant at 300° C. with complete recovery on cooling, thereby evidencing no hysteresis.

For comparative purposes, typical metal terephthalates having high volume resistivities of $10^{12}$ to $10^{14}$ ohm-cm and dielectric constants of between 4 and 5 were tested. These values are given by Ca, Zn, Mg, Al, In, Pb, Cd, Sn(II), Fe(III), Sr, Hg, Co, Ni and Cu(II) terephthalates. Wherefore, it is surprising that stannic terephthalate has an unusually high dielectric constant and more so that this constant is highly stable with regard to applied voltages and incident temperature. The combination of high dielectric constant, electrical and thermal stability, and high volume resistivity make this compound ideal for use as a capacitor dielectric.

What is claimed is:
1. Stannic terephthalate.

* * * * *